United States Patent [19]

Minagawa et al.

[11] 4,225,474

[45] Sep. 30, 1980

[54] ORGANOPHOSPHONATE COESTER STABILIZERS

[75] Inventors: Motonobu Minagawa, Kosigaya; Yutaka Nakahara, Iwatsuki; Masayuki Takahashi, Tokorozawa, all of Japan

[73] Assignee: Argus Chemical Corp., Brooklyn, N.Y.

[21] Appl. No.: 874,376

[22] Filed: Feb. 2, 1978

[30] Foreign Application Priority Data

Feb. 4, 1977 [JP] Japan .................................. 52/11258

[51] Int. Cl.² .......................... C07C 69/96; C08K 5/52
[52] U.S. Cl. .......................... 260/23 XA; 260/45.95 R; 260/45.95 C; 260/463; 252/404
[58] Field of Search ......... 260/463, 45.95 R, 45.95 C, 260/953, 928, 23 XA; 252/404

[56] References Cited

U.S. PATENT DOCUMENTS

| | | | |
|---|---|---|---|
| 2,999,841 | 9/1961 | Csendes | 260/45.95 E |
| 3,026,264 | 3/1962 | Rocklin | 260/45.95 B |
| 3,239,484 | 3/1966 | Stark | 260/45.95 B |
| 3,244,650 | 4/1966 | Hecker | 260/23 H |
| 3,404,122 | 10/1968 | Fritz | 260/47 XA |
| 3,433,225 | 7/1969 | Pollock | 260/23 XA |
| 3,544,514 | 12/1970 | Schnell et al. | 260/47 XA |
| 3,737,486 | 6/1973 | Schutze et al. | 260/45.95 D |
| 3,869,423 | 3/1975 | Minagawa et al. | 260/45.8 NT |

OTHER PUBLICATIONS

Polymer Engineering and Science, Jul. 1966, pp. 231 to 239, Article by Gordon et al.

*Primary Examiner*—V. P. Hoke
*Attorney, Agent, or Firm*—Otto S. Kauder

[57] ABSTRACT

New polyhydric phenol coesters are disclosed of polyhydric phenols, having 2 to 3 phenolic hydroxyl groups and 1 to 3 benzenoid rings, with carbonic acid and an organophosphonic acid having linked to phosphorus as alkyl, aryl, aralkyl or alkaryl group optionally substituted with a phenolic hydroxyl group. The new coesters have molecular weights up to a maximum of about 10,000, preferably from 1000 to 9000, and are highly effective stabilizers for a variety of synthetic resins.

Stabilizer compositions comprising a polyhydric phenol coester and a known polymer stabilizer, as well as synthetic resins stabilized with such stabilizer compositions, are also disclosed.

16 Claims, No Drawings

ORGANOPHOSPHONATE COESTER STABILIZERS

BACKGROUND OF THE INVENTION

This invention relates to a new class of polyhydric phenol coesters and to synthetic resin stabilizer compositions comprising these coesters as well as to synthetic resins stabilized with such coesters and with stabilizer compositions comprising these coesters along with known polymer stabilizers.

The usefulness of phenols in stabilizer compositions for synthetic resins are recognized early in the development of polymer stabilization by additives, as disclosed for example by F. Duggan in U.S. Pat. No. 2,126,179 of Aug. 9, 1938, W. Leistner in U.S. Pat. No. 2,564,646 of Aug. 14, 1951, and W. Fischer in U.S. Pat. No. 2,625,521 of Jan. 13, 1953, in the stabilization of polyvinyl chloride resin compositions. Over the years, phenolic stabilizers have been used in an expanding variety of synthetic resins and an enormous number of disclosures of new phenolic stabilizers has accumulated. Rather than attempt to list every one of these disclosures, A. DiBattista in U.S. Pat. No. 3,824,192 of July 16, 1974 and M. Minagawa in U.S. Pat. No. 3,849,370 of Nov. 19, 1974 and in U.S. Pat. No. 3,869,423 of Mar. 4, 1975 are cited as summaries of a very large part of the existing art of phenolic stabilizers.

Phenolic stabilizers are also employed in conjunction with other stabilizers such as esters of thiodipropionic acid or organic phosphites in the stabilization of polypropylene and other synthetic resins against degradation upon heating or ageing under atmospheric conditions. Disclosures by C. Tholstrup, U.S. Pat. No. 3,033,814 of May 8, 1962 and U.S. Pat. No. 3,160,680 of Dec. 8, 1964; L. Rayner, U.S. Pat. No. 3,181,971 of May 4, 1965; D. Bown, U.S. Pat. No. 3,242,135 of Mar. 22, 1966; S. Murdock, U.S. Pat. No. 3,245,949 of Apr. 12, 1966; H. Hagemeyer, U.S. Pat. No. 3,282,890 of Nov. 1, 1966; J. Casey, U.S. Pat. No. 3,496,128 of Feb. 17, 1970 and U.S. Pat. No. 3,586,657 of June 22, 1971; M. Minagawa, U.S. Pat. No. 3,549,572 of Dec. 22, 1970, and U.S. Pat. No. 3,629,189 of Dec. 21, 1971, and U.S. Pat. No. 3,673,152 of June 27, 1972, U.S. Pat. No. 3,849,370 of Nov. 19, 1974 and U.S. Pat. No. 3,869,423 of Mar. 4, 1975; W. Drake U.S. Pat. No. 3,624,026 of Nov. 30, 1971; A. DiBattista, U.S. Pat. No. 3,824,192 of July 16, 1974; B. Cook, U.S. Pat. No. 3,850,877 and H. Mueller U.S. Pat. No. 3,850,918 of Nov. 26, 1974; M. Dexter U.S. Pat. Nos. 3,856,748 of Dec. 24, 1974, and U.S. Pat. No. 3,888,824 of June 10, 1975, and U.S. Pat. No. 3,903,160 of Sept. 2, 1975; P. Klemchuk of U.S. Pat. No. 3,860,558 of Jan. 14, 1975; M. Rasberger U.S. Pat. No. 3,867,340 of Feb. 18, 1975 and U.S. Pat. No. 3,901,931 of Aug. 26, 1975; H. Brunetti U.S. Pat. No. 3,867,337 of Feb. 18, 1975 and U.S. Pat. No. 3,873,498 of Mar. 25, 1975; S. Rosenberger U.S. Pat. No. 3,884,874 of May 20, 1975 and U.S. Pat. No. 3,887,518 of June 3, 1975; C. Ramey U.S. Pat. No. 3,907,803 of Sept. 23, 1975 are representative of a very large number of stabilizer combinations including dilauryl and distearyl thiodipropionate or other dialkyl thiodipropionates along with polyhydricphenols and sometimes organic phosphites, metallic stearates, ultraviolet absorbers, nickel compounds, and heavy metal deactivators for use in polypropylene and other polyolefins.

Disclosures by R. Werkheiser, U.S. Pat. No. 2,726,226 of Dec. 6, 1975; I. Salyer et al, U.S. Pat. No. 2,985,617 of May 23, 1961; L. Friedman, U.S. Pat. No. 3,039,993 of June 19, 1962; W. Nudenberg, U.S. Pat. No. 3,080,338 of Mar. 5, 1963; C. Fuchsman, U.S. Pat. No. 3,082,187 of Mar. 19, 1963; H. Orloff et al, U.S. Pat. No. 3,115,465 of Dec. 24, 1963; A. Nicholson, U.S. Pat. No. 3,167,526 of Jan. 26, 1975; A. Hecker et al, U.S. Pat. No. 3,149,093 of Sept. 15, 1964, U.S. Pat. No. 3,244,650 of Apr. 5, 1966 and U.S. Pat. No. 3,225,136 and U.S. Pat. No. 3,255,151 of June 7, 1966; C. Bawn, U.S. Pat. No. 3,352,820 of Nov. 14, 1967; D. Miller, U.S. Pat. No. 3,535,277 of Oct. 20, 1970; J. Casey, U.S. Pat. No. 3,586,657 of June 22, 1971; C. Abramoff U.S. Pat. No. 3,856,728 of Dec. 24, 1974; M. Minagawa, U.S. Pat. No. 3,869,423 of Mar. 4, 1975 and U.S. Pat. No. 3,907,517 of Sept. 23, 1975; and British Pat. Nos. 846,684, 851,670, and 866,883 are representative of stabilizer combinations including organic phosphites, polyhydric phenols, and other active ingredients.

As summarized in a publication by D. Plank and J. Floyd (title—"Polycarbonates: A New Concept in Stabilization for Polypropylene", meeting preprints, Society of Plastics Engineers, Houston, Texas, April 1975; pages 33-37), there have long been several problems with using phenols as stabilizers despite their widespread use. Many phenol stabilizers are volatilized out of the polymer at high use temperatures. Some phenol stabilizers are extractable under certain use conditions. The oxidative products of most phenols are highly colored, thus imparting a yellow color to the polymer. Many phenols are reactive towards acidic or basic residues in the polymer. Following are disclosures of suggested ways to overcome these problems.

L. Friedman has disclosed in U.S. Pat. No. 3,053,878 of Sept. 11, 1962 a class of linear phosphite polymers having the formula

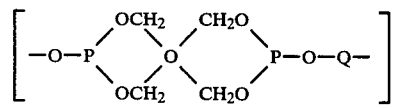

in which Q is the alkylene or arylene portion of a dihydric alcohol or dihydric phenol. R. Morris et al. in U.S. Pat. No. 3,112,286 of Nov. 26, 1963 disclosed phosphites having the formula

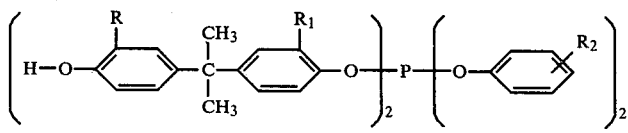

in which R represents a bulky hydrocarbon group such as t-butyl, t-amyl, t-hexyl, cyclohexyl, t-pentyl, t-octyl, phenyl, and the like: $R_1$ represents hydrogen and R; $R_3$ represents an alkyl group from 6 to 20 carbon atoms which is preferably in the meta or para position; x represents a number of from 1 to 3 inclusive; y represents a number of from 0 to 2 inclusive and the sum of the numerical value of x+y is always exactly 3.

D. Brown, U.S. Pat. No. 3,297,631 of Jan. 10, 1967 disclosed condensation products of phosphorus compounds with bisphenols and trisphenols which may be represented by the structures:

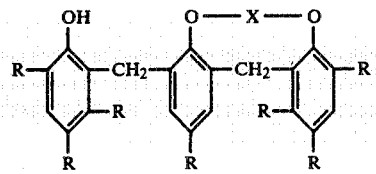

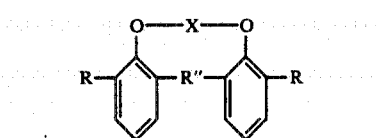

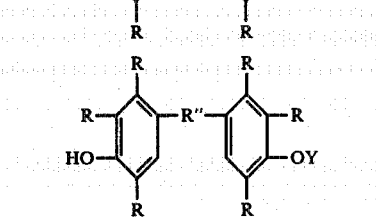

Where:

X is selected from the following:

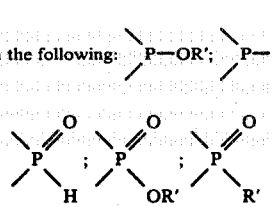

and Y is selected from the following: —P(OR')$_2$;

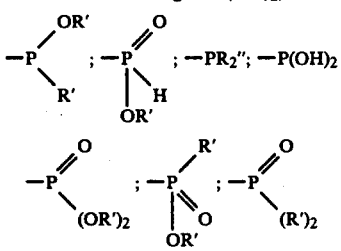

R is hydrogen, alkyl of 1 to 16 carbon atoms or aryl or a combination of these; R' is alkyl of 1 to 16 carbon atoms or aryl, and R" is alkylidene of 1 to 16 carbon atoms or an aryl-substituted alkylidene. C. Baranauckas, U.S. Pat. No. 3,305,608 of Feb. 21, 1967, disclosed phenolic phosphites useful as polymer stabilizers prepared by reacting a triorganophosphite, a polyol, and an aromatic material having two to six phenolic hydroxyl groups at 60°–180° C. in specified proportions.

G. Brindell, U.S. Pat. No. 3,412,064 of Nov. 19, 1968 disclosed phenolic phosphites represented by the general formula:

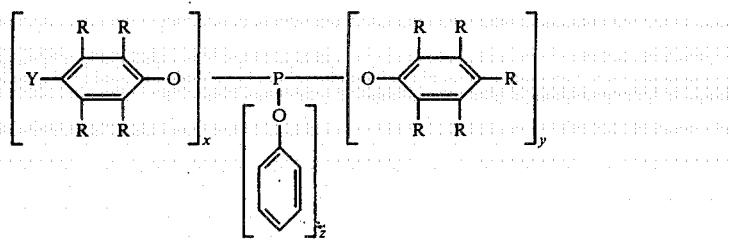

where x is from 1 to 3, y and z each from 0 to 2, x+y+z=3, R is hydrogen or alkyl and Y is hydroxyl or a group of the formula

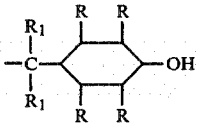

where R is hydrogen or alkyl M. Larrison, U.S. Pat. No. 3,419,524 of Dec. 31, 1968, disclosed phosphites useful as polymer stabilizers having the formula:

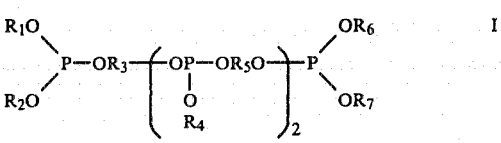

where $R_1, R_2, R_4, R_6,$ and $R_7$ are aryl or haloaryl, and $R_3$ and $R_5$ are a polyalkylidene glycol or an alkylidene bisphenol or a hydrogenated alkylidene bisphenol or a ring halogenated alkylidene bisphenol from which the two terminal hydrogens have been removed. O. Kauder et al, U.S. Pat. No. 3,476,699 of Nov. 4, 1969 and U.S. Pat. No. 3,655,832 of Apr. 11, 1972 disclosed organic phosphites containing a free phenolic hydroxyl group and defined by the formula:

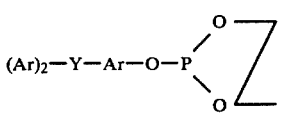

wherein Z is selected from the group consisting of hydrogen and aliphatic, cycloaliphatic, aromatic, heterocyclic and $(Ar)_p$—Y—Ar groups, taken in sufficient number to satisfy the valences of the two phosphite oxygen atoms; Y is a polyvalent linking group selected from the group consisting of oxygen; aliphatic, cycloaliphatic and aromatic hydrocarbon groups attached to each Ar group through a carbon atom not a member of an aromatic ring; oxyaliphatic; thioaliphatic, oxycycloaliphatic, thiocycloaliphatic; heterocyclic; oxyheterocyclic, thioheterocyclic, carbonyl, sulfinyl; and sulfonyl groups; Ar is a phenolic nucleus which can be phenyl or a polycarbocyclic group having condensed or separate phenyl rings; each Ar group is either connected through an oxygen atom to a phosphite group or contains a free phenolic hydroxyl group, or both; and p is a number, one or greater, and preferably from one to four, which defines the number of Ar groups linked to Y.

L. Friedman, U.S. Pat. No. 3,516,963 of June 23, 1970, disclosed phosphites having the formula:

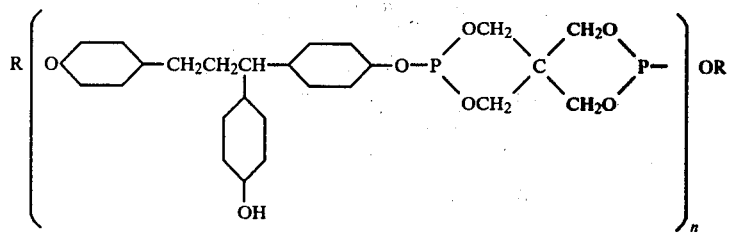

where R is alkyl, alkenyl, aryl, aralkyl, haloaryl, haloalkyl or

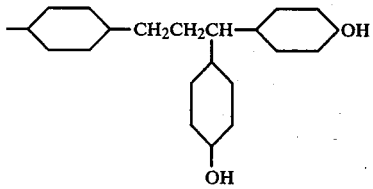

and n is an integer of at least 1. n can be 2, 3, 4, 5, 6, 7, 8, 10, 50, 100 or even more.

D. Bown et al. in U.S. Pat. No. 3,510,507 of May 5, 1970 and U.S. Pat. No. 3,691,132 of Sept. 12, 1972 disclosed polyolefins stabilized with polyphosphites, polyphosphates, polyphosphonites, polyphosphonates, polyborates, polycarbonates, and polysilanes which are condensation products of a 4,4'-bisphenol with a condensing or linking agent which may be of the ester type, such as the esters of triaryl or mixed aryl-alkyl compounds, or the acid halide type. Bown's condensation product stabilizers have molecular weights between 600 and 8000 or higher and are described by the structural formula,

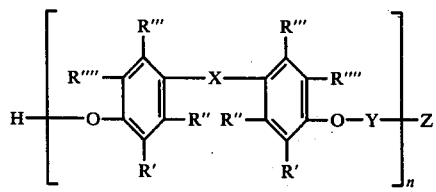

where X is selected from the group consisting of

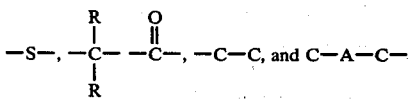

where

A is a $C_1$ to $C_{16}$ alkylene or an arylene;

R', R", R''', and R'''' are selected from the group consisting of hydrogen, $C_1$ to $C_{18}$ alkyls, and an aryl group; Y is selected from the group of

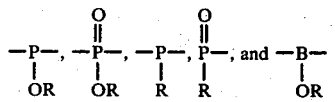

where R is hydrogen, a $C_1$ to $C_{18}$ alkyl, or aryl;

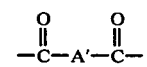

where m is 0 to 10, preferably 4 to 8,

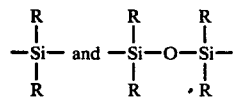

where A' is $(CH_2)_n$—S—$(CH_2)_n$ or —$(CH_2)_n$—S—$(CH_2)_m$—.

S—$(CH_2)_n$ where n is 0 to 10, preferably 2 and m is 0 to 10, preferably 5;

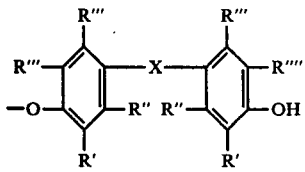

where R is an alkyl, preferably methyl, and Z is

where R', R", R''', R'''', and X correspond respectively to the R',R",R''',R'''', and X previously selected when n has a value from 1 to 15, or Z may be derived from the compound used to introduce Y into the product when n has a value from 2 to 15, for example —R or —OR where R is hydrogen, an alkyl, or aryl. When Y in the formula of Bown's stabilizer is $$-\underset{\underset{OR}{|}}{P}-,$$

the stabilizer is a type of hydroxyaryl phosphite. Similarly, when Y in the formula is

the stabilizer is a hydroxyaryl carbonate.

Bown's condensation products are described as especially effective in high molecular weight solid polyolefins when used together with a dialkyl sulfide costabilizer such as dilauryl thiodipropionate, distearyl thiodipropionate, ditridecyl thiodipropionate, dicetyl sulfide, bis(tetradecylmercapto)paraxylylene, and 10,24-dithiotetracontane. J. Floyd et al in J. S. U.S. Pat. No. 4,032,510 of June 28, 1977 disclosed low molecular weight polycarbonate esters of bisphenols such as 2,2-bis(3-t-butyl-4-hydroxyphenylpropane) and 4,4'-butylidene bis(6-t-butyl-3-methylphenol) prepared in such a way as to contain few or no free phenolic hydroxyl groups as being highly effective heat and light stabilizers for polyolefins and giving a synergistic effect with distearyl thiodipropionate, tris (nonylphenyl)phosphite, and distearyl pentaerythritoldiphosphite.

D. Plank and J. Floyd in the 1975 publication already cited have disclosed two general synthetic procedures for preparing stabilizer polycarbonates. They may be obtained by direct phosgenation of a bisphenol either in methylene chloride with pyridine as a catalyst or directly in pyridine. Using this procedure, a typical product obtained has the following formula.

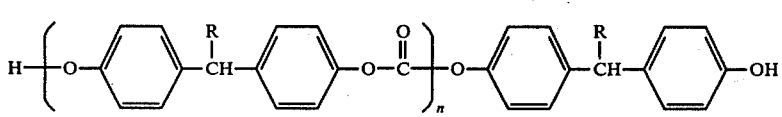

The authors did not state the nature of R or a value of n but did indicate that the molecular weight can be controlled easily by adding a modifier to the reaction mixture. The nature of the modifier is not mentioned. The authors disclosed a range of molecular weights from 680 to 1952, with the highest molecular weight products providing the longest 150° C. oven life in polypropylene also containing a thioester, distearyl thiodipropionate. The authors stated that when used alone, two products within their class of polycarbonates are not effective stabilizers, but they formed a very effective stabilizing system in combination with a thioester.

In other disclosures of polyhydric phenol carbonate ester additives to synthetic resin compositions, H. Peters in German Pat. No. 1,146,251 of Mar. 28, 1963 improved mechanical properties of polyolefins by adding 0.5 to 50% 2,2bis(4-hydroxyphenylpropane)carbonic acid polyester. T. Saito in U.S. Pat. No. 3,364,281 of Jan. 16, 1968 disclosed polyolefin fibers of improved dyeability containing 1 to 20% of polymeric additive which can be a high molecular weight polyhydric phenol carbonate. Solvay et Cie. in British Pat. No. 1,135,976 of Dec. 11, 1968 has disclosed the use of a high molecular weight bis(hydroxyphenyl)propane-phosgene condensation product as an adjunct to the polymerization initiator for the polymerization of ethylene. I. Ouchi in Japanese Patent 69-21,676 of Sept. 16, 1969 improved the smoothness of polyethylene terephthalate film by incorporating a small percentage of polycarbonate. Z. Opritz in U.S.S.R. Pat. No. 314,827 of Sept. 21, 1971 disclosed improved heat resistance of polyamides prepared from amino acids or lactams by addition of up to 10% of a polycarbonate having a formula $(OC_6H_4RC_6H_4O_2C)_x$ where R is $CH_2$, $CMe_2$, or $C(C_nH_{2n+1})_2$. Y. Umezawa in Japanese Kokai 72-34,744 of Nov. 22, 1972 disclosed styreneacrylonitrile copolymer compositions having improved moldability and mechanical properties with 5 to 40% polycarbonate resin. None of these disclosures relates to a coester of a polyhydric phenol with carbonic acid and a dicarboxylic acid or to a carbonate ester of molecular weight less than 10,000.

Carbonate esters and carbonate-dicarboxylic acid coesters of polyhydric phenols are known in the form of high molecular weight materials that are useful as films, fibers, molded or extruded parts and surface coatings for use in structural, decorative and electrical applications. The extensive literature has been reviewed by L. Bottenbruch in "Encyclopedia of Polymer Science and Technology" (N. Bikales, ed.) Volume 10, pages 714–725 (J. Wiley-Interscience Publishers, New York 1969). High molecular weight coesters including aliphatic dicarboxylic acids in the polymer chain with polyhydric phenol carbonates have been disclosed by E. Goldberg, in U.S. Pat. Nos. 3,020,331 and 3,030,335 of Apr. 17, 1962, U.S. Pat. No. 3,161,615 of Dec. 15, 1964, U.S. Pat. No. 3,169,121 of Feb. 9, 1965, and U.S. Pat. No. 3,207,814 of Sept. 21, 1965. N. Reinking in U.S. Pat. No. 3,166,606 of Jan. 19, 1965 and H. Schnell in U.S. Pat. No. 3,553,167 of Jan. 5, 1971.

SUMMARY OF THE INVENTION

In accordance with this invention, new polyhydric phenol coesters of polyhydric phenols having 2 to 3 phenolic hydroxyl groups and 1 to 3 non-condensed benzenoid rings with carbonic acid and an organophosphonic acid having linked to phosphorus through carbon an organic group having 1 to about 25 carbon atoms and not more than one phenolic hydroxyl group are prepared. The coesters have molecular weights ranging up to a maximum of about 10,000, preferably from 1000 to about 9000 for highest effectiveness as ingredients of stabilizer compositions for synthetic resins. The molar proportions of the organophosphonic acid to the carbonic acid in the coester range from 20:1 to 1:20, preferably from 4:1 to 1:4. The coesters of the invention can contain a single polyhydric phenol or a plurality of polyhydric phenols as well as a single organophosphonic acid or a plurality of organophosphonic acids. The terms "organophosphonic" acid and "organophosphonate" ester are used to indicate acids and esters respectively characterized by phosphorus atoms each bonded to one carbon atom and three oxygen atoms. Synthetic resin stabilizer compositions comprising the coesters of this invention contain at least one known polymer stabilizer along with one or more coesters according to this invention. The proportions of coester to known polymer stabilizer in such stabilizer compositions can range from 1 to 1 to about 1 to 30 by weight.

A variety of synthetic resins is stabilized against the deleterious effects of heat or light by incorporating therein 0.001 to 5 parts by weight per 100 parts of synthetic resin of a coester according to this invention.

DESCRIPTION OF PREFERRED EMBODIMENTS

Essential to the achievement of the unexpected effectiveness in resin stabilizer compositions of the coesters of this invention are the presence in the molecule of both carbonate and organophosphonate ester structures and controlled molecular weight of the polyhydric phenol organophosphonic acid and carbonic acid coesters. There results from these essential features a minimal volatility and leachability so that the stabilizing effectiveness manifested by the coesters is maintained over long periods of time where resin compositions stabilized with the coesters are exposed to the action of air, water, and chemical solutions at an elevated temperature.

The polyhydric phenol organophosphonate carbonate coesters of this invention are derived from carbonic acid, introduced into the molecule by a carbonylating agent such as an ester or acid chloride of carbonic acid; at least one organophosphonic acid introduced into the molecule by way of an ester or acid chloride of the organophosphonic acid; and a polyhydric phenol having two to three hydroxyl groups and one to three non-condensed benzenoid rings which can be substituted with up to three alkyl, cycloalkyl, or aralkyl groups having 1 to 10 carbon atoms. Organophosphonic acid-carbonic acid coesters of polyhydric phenols having a hydrocarbon substituent such as t-butyl or cyclohexyl positioned ortho to the phenolic hydroxyl in each benzenoid ring of the polyhydric phenol are preferred.

The polyhydric phenol carbonate-organophosphonate coesters of this invention are crystalline powders or grindable glassy solids. Unlike the many known polyhydric phenol carbonate resins and plastics, the coesters of the invention have by themselves no useful mechanical strength, which is probably a result of the entirely different molecular weight range of the coesters of this invention as contrasted to known polyhydric phenol carbonate esters whose molecular weight for useful mechanical strength in fibers, films, etc., ranges from a 30000 minimum to above 100000.

The organophosphonic acids from which the polyhydric phenol carbonate-organophosphonate coesters of this invention are derived can be alkanephosphonic acids, cycloalkanephosphonic acids, arylalkanephosphonic acids, aromatic hydrocarbonphosphonic acids, and alkylaromatic hydrocarbonphosphonic acids in which the alkane, cycloalkane, arylalkane, aromatic hydrocarbon, and alkylaromatichydrocarbon groups are linked to phosphorus through carbon. The arylalkanephosphonic acids, aromatic hydrocarbonphosphonic acids, and alkyl aromatic hydrocarbonphosphonic acids can carry one phenolic hydroxyl group in the group linked to phosphorus through carbon.

Alkanephosphonic acids have from 1 to about 25 carbon atoms and include methanephosphonic acid, ethanephosphonic acid, n-butanephosphonic acid, isopentanephosphonic acid, 2-ethylhexanephosphonic acid, 3,4-dimethylhexanephosphonic acid, n-decanephosphonic acid, n-hexadecanephosphonic acid, n-eicosanephosphonic acid, tetracosanephosphonic acid, and alkanephosphonic acids in which the alkane group is the residue of an oxo process derived alcohol such as "isodecyl", "isotridecyl", and "isohexadecyl".

Cycloalkanephosphonic acids have from 5 to about 25 carbon atoms and include cyclopentanephosphonic acid, methylcyclopentanephosphonic acid, cyclohexanephosphonic acid, t-butylcyclohexanephosphonic acid, cyclohexylcyclohexanephosphonic acid and cyclododecanephosphonic acid.

Aromatic hydrocarbonphosphonic acids have from 6 to about 25 carbon atoms and include benzenephosphonic acid, naphthalenephosphonic acid, diphenylbenzenephosphonic acid, and phenanthrenephosphonic acid and monophenolic derivatives thereof.

Arylalkanephosphonic acids and alkylaromatic hydrocarbonphosphonic acids have 7 to about 25 carbon atoms and include p-toluenephosphonic acid, benzylphosphonic acid, 1-phenylethanephosphonic acid xylene-phosphonic acid, 6-phenylhexanephosphonic acid, dodecylbenzenephosphonic acid, p-dodecylbenzylphosphonic acid, dinonylbenzenephosphonic acid, and monophenolic derivatives such as 3-methyl-4-hydroxy-5-t-butylbenzylphosphonic acid.

In the polyhydric phenol organophosphonate-carbonate esters of this invention, each organophosphonic acid group is linked to two esterifying groups, of which at least one is a polyhydric phenol group. The second esterifying group can be a polyhydric phenol group, as well as an alkyl, cycloalkyl, aryl, alkaryl or aralkyl group having up to about 25 carbon atoms.

Phosphorus-carbon linked organophosphonic acids and esters are known and have been reviewed by G. M. Kosolapoff in "Organophosphorus Compounds" (J. Wiley, New York, 1950) pages 150–167 as well as by in Houben-Weyl "Methoden der Organischen Chemie" (G. Thieme Verlag, Stuttgart, Germany 1963, Vol. 12 Part 1, pgs. 338–550. Nomenclature, structure, properties, and synthetic methods are described.

A preferred class of polyhydric phenol carbonate organophosphonate coesters of this invention is derived from carbonic acid with an organophosphonic acid and orthosubstituted 1,3-and 1,4-dihydric phenols having one benzenoid ring such as 2,5-di-t-butyl-hydroquinone, 2,3,6-trimethylhydroquinone, 2-methylresorcinol, and 2,6-di-t-butylresorcinol.

Also useful polyhydric phenol carbonate-organophosphonate coesters are coesters of ortho-substituted bisphenols having two ortho-substituted phenolic groups linked directly or through a two valent hydrocarbon group such as 2,2'-methylene bis(4-methyl-6-t-butyl-phenol), 2,2'-methylene bis(4-ethyl-6-t-butylphenol), 2,2'-n-butylidene bis(4,6-dimethylphenol), bis-1,1-(2'-hydroxy-3',5'-di-methylphenyl)-3,5,5-trimethylhexane, 2,2'-cyclohexylidene bis(4-ethyl-6-t-butylphenol), 4,4'-bis(2,6-di-t-butylphenol), 4,4'-methylene bis-(2,6-di-t-butylphenyl), 4,4'-isopropylidene bis(2-phenylethylphenol), 4,4'-n-butylidene bis(3-methyl-6-t-butylphenol), 4,4'-cyclohexylidene bis(2-t-butylphenol), 4,4'-cyclohexylidene bis(2-cyclohexylphenol), and 4,4'-benzylidene bis(2-t-butyl-5-methylphenol).

Another preferred class of polyhydric phenol carbonate-organophosphonate coesters provided in accordance with this invention is the class of carbonate coesters of ortho-substituted bisphenols having two ortho-substituted phenolic groups linked through oxygen or sulfur, such as 4,4'-oxobis(3-methyl-6-isopropylphenol), 4,4'-thiobis(2-methyl-6-t-butyl phenol), 4,4'-thiobis(3-methyl-6-t-butylphenol), 4,4'-sulfobis(3-methyl-6-t-butylphenol), bis(2-methyl-4-hydroxy-5-t-butylbenzyl) sulfide, bis(3,5-di-t-butyl-4-hydroxybenzyl) sulfide, 2,2'-thiobis(4-hydroxybenzyl) sulfide, 2,2'-thiobis(4-t-butyl-6-methylphenol), 2,2'-thiobis-(4,6-di-t-butylphenol).

A particularly preferred class of polyhydric phenol carbonateorganophosphonate coesters is the class of carbonate coesters of ortho-substituted trisphenols having three ortho-substituted phenol groups, such as 1,1,3-tris(2'-methyl-4'-hydroxy-5'-t-butylphenyl)butane, 1,3,5-tris(3',5'-di-t-butyl-4'-hydroxybenzyl)-2,4,6-trimethylbenzene, 2,2-bis-(3'-t-butyl-4'-hydroxyphenyl)-4-(3",5"-di-t-butyl-4"-hydroxyphenyl)butane, and 2,2-bis(2'-methyl-5-t-butyl-4'-hydroxyphenyl)-4-(3",5"-di-t-butyl-4"-hydroxyphenyl)butane.

The most preferred class of polyhydric phenol carbonateorganophosphonate coesters of this invention can be represented by the formula

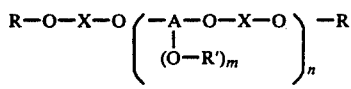

in which R is an alkyl, cycloalkyl, aralkyl, aryl, or alkaryl group having up to about 25 carbon atoms as defined above, or the group $-A-(OH)_{m+1}$; X independently at each occurrence is a carbonyl

group or an organophosphonyl

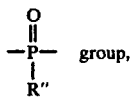

provided that at least one X is

and at least one X is

A is a residue of a dihydric or trihydric phenol preferably carrying at least one ortho-alkyl substituent of the kind defined above; R' is a hydrogen atom or the group $-X-O-R$; R" is the organic group linked to phosphorus through carbon, i.e. alkyl, cycloalkyl, aralkyl, aryl, or alkaryl having up to about 25 carbon atoms as defined above or the group

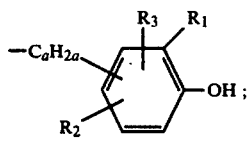

$R_1$ is an alkyl group, $R_2$ and $R_3$ are each independently hydrogen or alkyl groups; a is an integer from 1 to 8, m is zero or one, and n is an integer from 1 to 20. When occurring more than once in this formula, R, R', R", $R_1$, $R_2$, $R_3$ and A can be the same or different at each occurrence. When A is derived from a dihydric phenol, m is zero and when A is derived from a trihydric phenol m is one.

The polyhydric phenol organophosphonate-carbonate coesters of this invention can be prepared by the reaction of a carbonylating agent such as phosgene, a chloroformate ester, a dialkyl carbonate or a diaryl carbonate with an organophosphonic acid compound and a substituted dihydric or trihydric phenol in one or several reaction stages. Acid acceptors such as ammonia, pyridine, organic amines, and inorganic alkalies can be used with phosgene and chloroformate esters, and acidic or alkaline transesterification catalysts can facilitate the reaction of alkyl and aryl carbonate esters. The molecular weight of the coester is regulated by the proportions of organophosphonic acid compound and carbonylating agent to dihydric or trihydric phenol. The more closely the proportions of the combined organophosphonic acid and carbonylating agent to dihydric or trihydric phenol approach one to one compound equivalent of each reactant the higher the molecular weight of the resulting product.

Conversely, either reactant can be used in large excess to prepare products having nearly the lowest molecular weight possible, that is a coester having a single carbonate ester group, a single organophosphonic acid ester group, and the minimum number of a polyhydric phenol groups to link these together. Thus the product of the reaction between two moles of a dihydric phenol and one mole of carbonylating agent is a relatively low molecular weight mixture of carbonate esters in which the bis(hydroxyaryl carbonate) of the dihydric phenol predominates, and the product of the reaction between two moles of a carbonate ester carbonylating agent (e.g. diphenyl carbonate) and one mole of dihydric phenol is a relatively low molecular weight mixture of carbonate esters in which the dihydric phenol bis(phenyl carbonate) ester predominates.

Each of these products can then be used to prepare a coester of this invention by reaction with an appropriate organophosphonic acid compound. Thus the above bis(hydroxyaryl) carbonate ester of the polyhydric phenol can be caused to condense with the acid chloride or phenyl ester of an organophosphonic acid, with elimination of hydrogen chloride or phenol as side product respectively, to give a carbonate organophosphonate coester with a molecular weight depending on the relative proportions of reactants. Similarly, a polyhydric phenol phenyl carbonate ester can be transesterified with a hydroxyaryl ester of an organophosphonic acid to displace phenol and give a carbonate-organophosphonate coester of the polyhydric phenol present in each of the starting materials, which means that the coester can be made up of different polyhydric phenols if each of the starting materials contains a different polyhydric phenol. Both techniques just described are essentially two stage reaction techniques that yield coesters of a relatively ordered structure in which polyhydric phenol groups are alternatingly linked through carbonate ester groups and through organophosphonate ester groups. Coesters prepared at elevated temperature, such as by the phenol ester transesterification technique, have the ordered alternating structure modified to a minor extent as a result of ester-ester interchange randomization. The reactions can be illustrated by equations in which for convenience the symbols HO—Ar—OH are used for the polyhydric phenols that can be used according to this invention, and R"PO(OPh)$_2$ and R″POCl$_2$ represent phenyl esters and acid chlorides of organophosphonic acids that can be used.

A. Condensation of hydroxyaryl carbonate with organophosphonic acid compound:

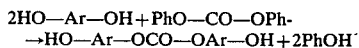

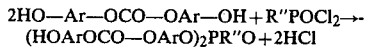

B. Condensation of phenyl carbonate of polyhydric phenol with an organophosphonic acid ester of a different polyhydric phenol:

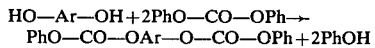

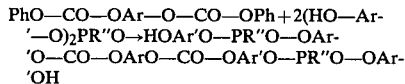

Both the phenyl ester reaction and the acid chloride reaction can be facilitated by the use of catalysts. The phenyl ester reaction is suitably catalyzed by substances of sufficient alkalinity to convert phenol at least in part to the phenoxide ion, such as alkali and alkaline earth metals and their oxides, hydroxides, sulfides, cyanides, phenolates, hydrides alcoholates, and carboxylates as well as aliphatic and cycloaliphatic amines, preferably tertiary amines to avoid the possible complication of amide formation. Suitable catalysts for the acid chloride reaction include tertiary amines, tertiary phosphines, and the hydrogen halide and alkyl halide addition salts thereof. Catalyst concentrations usefully range from 0.01% to about 5% by weight of reaction mixture. Preferred catalysts for the acid chloride reaction have the ability to partition between water and an immiscible hydrocarbon phase with a partition coefficient between 0.01 and 100.

Both the phenyl ester reaction method of preparing the coester of this invention and the acid chloride method can be carried out over a convenient range of reaction temperatures. The phenyl ester reaction is conveniently carried out at elevated temperatures of the order of 80° to 210° C. with removal of the side product phenol by distillation, suitably under diminished pressure. It is frequently helpful to begin the reaction by an atmospheric pressure cook, suitably with nitrogen or other inert gas protection over the reaction mass to preserve its light color, and apply vacuum gradually after a quantity of side product has accumulated for removal.

The acid chloride reaction is conveniently carried out at ambient temperatures or as cold as −15° C. Elevated temperatures in the 40° to 90° C. range can also be used.

In coesters prepared with an excess of equivalents of the dihydric or trihydric phenol reactant over the equivalents of carbonylating agent and organophosphonic acid compound combined, the coester is predominantly terminated by hydroxyaryl groups, while in coesters prepared with an excess of the combined equivalents of organophosphonic acid compound and carbonylating agent over the phenol, ester termination predominates. The hydroxyaryl terminated coesters having an average molecular weight ranging from 700 to about 10000 and especially with a molecular weight ranging from 1200 to about 7000 are preferred.

Synthetic resins that can be stabilized with compositions comprising a polyhydric phenol organophosphonate carbonate coester according to this invention include alphaolefin polymers such as polyethylene, polypropylene, polybutene, poly-3-methylbutene, or copolymers thereof such as ethylenevinylacetate copolymer, ethylenepropylene copolymer, polystyrene, polyvinylacetate, acrylic ester resins, copolymers from styrene and another monomer (for example, maleic anhydride, butadiene, acrylonitrile and so on), acrylonitrile-butadiene-styrene copolymer, acrylic acid ester-butadiene-styrene copolymer, methacrylic acid ester-butadiene-styrene copolymer, methacrylate ester resin such as polymethylmethacrylate, polyvinylalcohol, ethylene and butylene terephthalate polyesters, polyamide, polycarbonate, polyacetal, polyurethane, cellulosic resin, or phenolic resin, urea resin, melamine resin, epoxy resin, unsaturated polyester, silicone resin, halogen-containing resins such as polyvinyl chloride, polyvinylidene chloride, polyvinylidene fluoride and copolymers thereof, and further rubbers such as isoprene rubber, chloroprene rubber, and blends of the above resins.

Stabilizer compositions comprising a polyhydric phenol organophosphonate carbonate coester according to this invention can be formulated and marketed in liquid, solid, and paste forms. An inert solvent can be used to facilitate handling. The polyhydricphenol coester and known polymer stabilizers can also be solubilized in one another by heating, such as at 70°–160° C. for up to 4 hours, and then allowing the resulting melt to cool and harden sufficiently to be flaked and ground.

Known polymer stabilizers can be used in synthetic resin compositions together with the coester stabilizers of this invention and can be admixed with the latter. Such stabilizers include thiodipropionic acid esters, polyvalent metal salts of carboxylic acids, organic phosphites, 1,2-epoxides, polyhydric alcohols, polyhydric alcohol 3-alkylthiopropionic acid esters, ultraviolet stabilizers and heavy metal deactivators. Representative thiodipropionic acid esters include di-n-dodecyl thiodipropionate, di-hexadecyl thiodipropionate, distearyl thiodipropionate, n-octyl eicosanyl thiodipropionate and n-octadecyl cyclohexane-1,4-dimethanol thiodipropionate polyester. A comprehensive disclosure of useful thiodipropionate esters by M. Minagawa et al in U.S. Pat. No. 3,869,423, column 17 line 55 to column 19 line 54 is here incorporated by reference. When thiodipropionate esters are used the concentration based on 100 parts of polymer can range from 0.05 to about 0.75 parts by weight.

Representative polyvalent metal salts include zinc, calcium, magnesium, barium, strontium and nickel salts of monocarboxylic acids having 6 to 24 carbon atoms, for example zinc benzoate, calcium palmitate, and nickel 2-ethylbutyrate. A comprehensive disclosure of useful metal salts by M. Minagawa et al in U.S. Pat. No. 3,869,423, column 19 line 56 column 20 line 35 is here incorporated by reference. When metal salts are used the concentration based on 100 parts by weight of polymer can range from 0.1 to about 3 parts by weight.

Representative organic phosphites include triisodecylphosphite, tris (nonylphenyl phosphite), and 4,4′-isopropylidene diphenol alkyl (C$_{12}$–C$_{15}$) phosphite. A comprehensive disclosure of useful organic phosphites by M. Minagawa in U.S. Pat. No. 3,849,370 column 13 line 63 to column 16 line 48 is here incorporated by reference. Typical use concentrations of organic phosphites are in the range from 0.02 part to about 2 parts by weight per 100 parts of polymer being stabilized.

Representative 1,2-epoxides that can be used in stabilizer compositions according to this invention include epoxysoybean oil, epoxylinseed oil, and 2-ethylhexyl epoxystearate. A comprehensive disclosure of 1,2-epoxides by M. Minagawa et al in U.S. Pat. No. 3,869,423 column 26 line 13 to line 39 is here incorporated by reference. Typical use concentrations of 1,2-epoxides range from 0.3 to about 6 parts by weight per 100 parts of synthetic resin composition.

Aliphatic polyhydroxy compounds can be included with stabilizer compositions of this invention in amounts corresponding to 0.1 to about 1 part per 100 parts of polymer being stabilized. Typical aliphatic polyhydroxy compounds are glycerol, polyglycerol, mono-di-, and tri-pentaerythritol, mannitol, sorbitol, and partial esters of these with saturated and unsaturated fatty acids having 6 to 22 carbon atoms.

3-Alkylthio propionates of polyhydric alcohols can be included in stabilizer compositions of this invention in amounts corresponding to 0.02 to about 1 part per 100 parts of synthetic resin being stabilized. The propionate esters have 4 to about 34 carbon atoms in the alkylthiopropionate group, 2 to about 15 carbon atoms in the polyhydric alcohol group and 2 to about 8 ester group in the molecule. Representative propionate esters are 2,2-dimethylpropanediol bis(3-n-dodecylthio-2-methylpropionate), pentaerythritol tetrakis(3-n-octylthiopropionate) and tris(3-n-octadecylthiopropionyloxyethyl) isocyanurate. For a further listing of useful 3-alkylthiopropionates the disclosure of A. Onishi U.S. Pat. No. 3,629,194 can be consulted.

Ultraviolet stabilizers can be included in stabilizer compositions of this invention in amounts corresponding to 0.05 to about 1 part per 100 parts of synthetic resin being protected. Typical U V absorbing ultraviolet stabilizers are 2-hydroxybenzophenones such as 2-hydroxy-4-n-octyloxybenzophenone and 2,4-dihydroxybenzophenone, and 2-(2'hydroxyphenyl)benzotriazoles such as 2-(hydroxy-5'-methylphenyl) benzotriazole and 2-(2'-hydroxy-5'-t-butylphenyl) 5,6-dichlorobenzotriazole. For a further listing of many useful ultraviolet absorbers the disclosure of U.S. Pat. No. 3,395,112 of July 30, 1968, particularly column 14 line 40 to column 19 line 33, can be consulted.

Ultraviolet stabilizers that have little or no significant ultraviolet absorption and owe their effectiveness to a mode of action other than ultraviolet absorption include nickel or cobalt salts and complexes such as butylamine-nickel thiobis(p-octylphenol, nickel bis(N,N-dibutyldithiocarbamate), cobalt bis-(dicyclohexylphosphinodithioate), and the nickel alkyl phosphites of U.S. Pat. No. 3,395,112; aryl aromatic carboxylate esters such as bis(-nonylphenyl)isophthalate, resorcinol bis(t-butylbenzoate), and 2,4-di-t-butylphenyl 3,5-di-t-butyl-4-hydroxybenzoate; and, particularly preferred, derivatives of 2,2,6,6-tetralkylpiperidines including those disclosed by K. Murayama in U.S. Pat. Nos. 3,840,494 and 3,899,464 and by B. Holt in U.S. Pat. No. 4,021,432. The preferred tetralkylpiperidines that can be used together with the polyhydric phenol organophosphonate-carbonate coesters according to this invention are carboxylic acid esters of an alcohol linked to the 4 position of a 2,2,6,6-tetramethylpiperidine having 15 to 75 carbon atoms and a piperidine nitrogen content ranging from 2 to 8 percent by weight, and can be represented by the formula

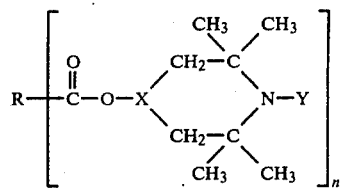

in which n is a whole number from 1 to 4, Y is selected from the group consisting of hydrogen and oxyl radical, X is a three valent linking member selected from the group consisting of —CH<,

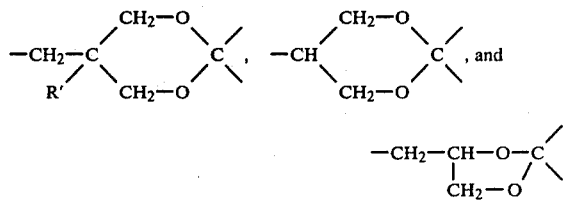

wherein R' is a lower alkyl group, and R is an organic group having a valence of n that can be open chain, carboxylic, and heterocyclic.

Lower alkyl R' groups include for example methyl, ethyl, propyl, isopropyl, n-butyl, and isobutyl. R groups can be for example alkyl such as ethyl, t-butyl, 2-heptyl, 1-undecyl, and 1-tricosanyl; aryl such as phenyl, t-butylphenyl, and 1-naphthyl; alkenyl such as allyl, methallyl, vinyl, propenyl, and 8-heptadecenyl; aralkyl such as benzyl and hydrocinnamyl; alkylene such as ethylene, 1,4-butylene, and decamethylene; alkenylene such as vinylene and 2-butene-1,4-diiyl; cycloalkylene and cycloalkenylene such as methylcyclopentylene, cyclohexenylene, and bicycloheptenylene; and heterocyclic groups such as furyl, thienyl, and pyrrolidonyl.

Specific examples of such 2,2,6,6-tetramethylpiperidines include bis(2,2,6,6-tetramethylpiperidin-4-yl) adipate, 2,2,6,6-tetramethylpiperidin-4-yl) 9,10-epoxystearate-1-oxyl radical, and tris(2,2,6,6-tetramethylpiperidine-4,4 (1:3'-dioxyisobutane-2-methyl))but-3-ene-1,2,3-tricarboxylate.

Stabilizer compositions according to this invention that protect synthetic resin compositions used in contact with materials containing heavy metals and their compounds, as in insulating materials for copper based electrical conductors or in compositions pigmented with heavy metal containing pigments such as rouge, talc, and iron-bearing asbestos, can contain heavy metal deactivators that counteract the prodegradant effect of the heavy metal on synthetic resin compositions that would be satisfactorily stabilized in the absence of heavy metal. Heavy metal deactivators that can be used in stabilizer compositions according to this invention include melamine, dicyandiamide, oxanilide, N,N'-disalicyloylhydrazine, 3-salicyloylamido-1,2,4-triazole, as well as the heavy metal deactivators disclosed by M. Minagawa in U.S. Pat. No. 3,549,572 (column 5 line 19 to column 10 line 23), U.S. Pat. No. 3,629,181 (column 5 line 15 to column 9 line 54), U.S. Pat. No. 3,673,152 (column 4 line 47 to column 8 line 62), and U.S. Pat. No. 3,849,370 (column 5 line 5 to column 13 line 45). These disclosures are here incorporated by reference.

Illustrative of stabilizer compositions comprising coesters of polyhydric phenols with carbonic acid and an organophosphonic acid according to this invention together with known polymer stabilizers are the following:

| STABI- LIZER COMPO- SITION | INGREDIENTS | PARTS BY WEIGHT |
|---|---|---|
| I | 2:1 (molar ratio) carbonate/ phenyl benzenephosphonate of 4,4'butylidenebis(3-methyl- 6-t-butylphenol), approx. mol. wt. 1600 | 10 |
| | Zinc Stearate | 20 |
| | Magnesium benzoate | 15 |
| | Mannitol | 25 |
| II | 2:3 carbonate/methyl methane- phosphonate of bis(3-methyl- 4-hydroxy-5-t-butylbenzyl) sulfide, approx. mol. wt. 1900 | 12 |
| | Barium nonylphenolate | 30 |
| | Zinc 2-ethylhexoate | 18 |
| | Diphenyl isodecyl phosphite | 40 |
| III | 2:5 carbonate/p-cresyl ethane- phosphonate of 3,5-dimethyl- hydroquinone, approx. mol. wt. 2900 | 25 |
| | 2-ethylhexyl epoxystearate | 45 |
| | tris(nonylphenyl) phosphite | 30 |
| IV | 4:3 carbonate/o-t-butylphenylbenzyl phosphonate of 4,4'-isopropyl- idenediphenol, approx. mol. wt. 2400 | 10 |
| | Strontium laurate | 80 |
| | Zinc laurate | 40 |
| | Dipentaerythritol | 15 |
| V | 1:1 carbonate/p-t-butyl cyclohexane- phosphonate of methylenebis(4,6-di-t- butylphenol) approx. mol. wt. 1800 | 25 |
| | Distearyl thiodipropionate | 45 |
| | Trihexadecyl phosphite | 10 |
| VI | 2:1 carbonate/2-ethylhexyl 2-ethyl- hexane phosphonate of t-butylhydroquin- one, approx. mol. wt. 2600 | 60 |
| | Dicyandiamide | 40 |
| VII | 3:1 carbonate/phenylbenzenephos- phonate of thiobis(2-t-butyl-5-methyl- phenol), approx. mol. wt. 3300 | 15 |
| | Pentaerythritol bis(n-octadecyl phosphite) | 6 |

The preparation of the stabilized resin composition is easily accomplished by conventional procedures. A heated two roll mill, for example, is a convenient compounding tool for blending stabilizer compositions of the invention with polyolefins, vinyl chloride polymers, ABS polymers, ethylenevinyl acetate copolymers and others.

The examples that follow illustrate the invention without limiting its scope. Synthetic Examples 1 and 2 describe the preparation of certain polyhydric phenol organophosphonic acid and carbonic ester coesters of this invention shown in Table 1 by techniques disclosed above. Examples 1-1 through 7-7 illustrate the use of coester stabilizers of this invention shown in Table 1 and stabilizer compositions comprising coesters of this invention shown in Table 1 in the stabilization of olefin polymers, a vinyl chloride polymer, an ABS polymer, and a butylene terephthalate polyester resin.

SYNTHETIC EXAMPLE 1

Synthesis of Table 1 No. 1 compound, phenyl 3,5-di-t-butyl-4-hydroxybenzyl phosphonate-carbonate of 4,4'-n-butylidene bis(2-t-butyl-5-methylphenol).

4,4'-n-Butylidenebis(2-t-butyl-5-methyl phenol) 114.6 g (0.3 mole), diphenyl carbonate 32.1 g (0.15 mole) and potassium carbonate 0.15 g were heated to 140°–145° C. under nitrogen atmosphere and then reacted for 2.5 hrs. After the reaction produced phenol was distilled out under reduced pressure. Diphenyl (3,5-di-t-butyl-4-hydroxy benzyl) phosphonate 135.6 g and sodium hydride 0.5 g were added and reacted at 170°–175° C. for 1 hour under nitrogen atmosphere and a further 4 hours at 170°–185° C. under reduced pressure while distilling out phenol. A glassy solid of melting point 120°–125° C. was obtained as residue.

SYNTHETIC EXAMPLE 2

Synthesis of Table 1 No. 3 compound phenyl 3,5-di-t-butyl-4-hydroxybenzyl phosphonate-carbonate of 1,1,3-tris(2'-methyl-4"-hydroxy-5'-t-butylphenyl)butane.

1,1,3-Tris(2'-methyl-4'-hydroxy-5'-t-butylphenyl)butane 109 g (0.2 mole), diphenyl carbonate 21.4 g (0.1 mole), diphenyl (3,5-di-t-butyl-4-hydroxy benzyl)phosphonate 181 g (0.4 mole) and sodium hydride 1.0 g were reacted at 170°–175° C. for 1.5 hr. under nitrogen atmosphere, and additional 4 hours, at 170°–185° C. while distilling out produced phenol. A glassy solid of melting point 126°–131° C. was obtained.

These and other polyhydric phenol carbonate-organophosphonate coesters of this invention are shown by name, formula, and average molecular weight in Table 1. Where no other molar ratio is indicated, the molar ratio of polyhydric phenol groups to carbonate ester groups is 2:1.

TABLE 1

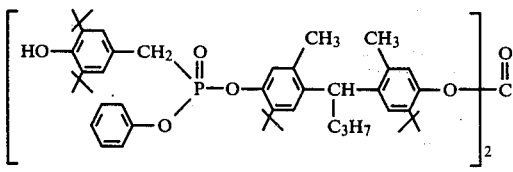

No. 1

Bis(O-phenyl-P(3,5-di-t-butyl-4-hydroxyphenylmethane)phosphonate of 4,4'-n-butylidenebis(2-t-butyl-5-methylphenol)) carbonate. M.P. 120–125° C., average molecular weight 1500

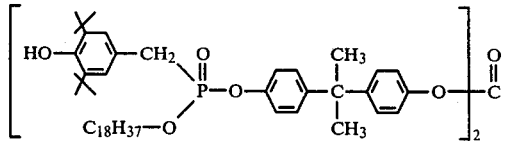

No. 2

TABLE 1-continued

Bis(O-n-octadecyl-P(3,5-di-t-butyl-4-hydroxyphenylmethane) phosphonate of 4,4′-isopropylidenediphenol)carbonate, average molecular weight 1600

No. 3

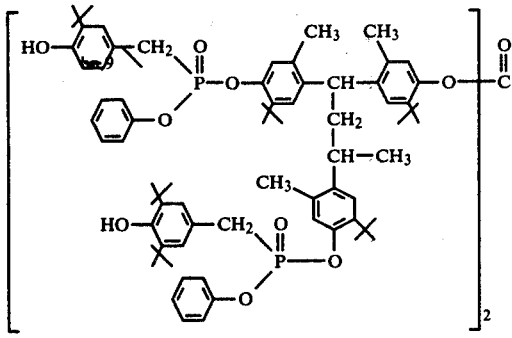

Bis(O-Phenyl-P(3,5-di-t-butyl-4-hydroxyphenylmethane)phosphonate of 1,1,3-tris(2-methyl-4-hydroxy-5-t-butylphenyl) butane) carbonate, Melting Point 126–131° C., average molecular weight 2600

No. 4

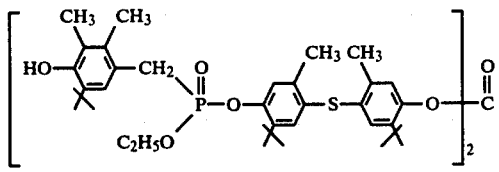

Bis(O-ethyl-P(2,3-dimethyl-4-hydroxy-5-t-butylphenylmethane) phosphonate of 4,4′-thiobis(2-t-butyl-5-methylphenol))carbonate average molecular weight 1300

No. 5

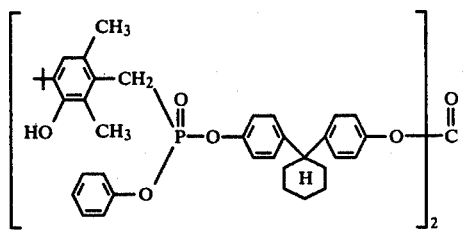

Bis(O-phenyl-P(2,6-dimethyl-3-hydroxy-4-t-butylphenylmethane) phosphonate of 4,4′-cyclohexylidenediphenol)carbonate, average molecular weight 1200

No. 6

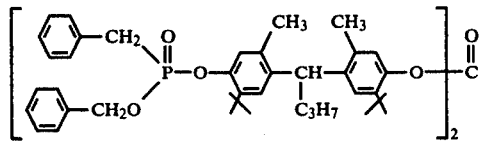

Bis(O-benzylP-phenylmethanephosphonate of 4,4′-n-butylidene-bis(2-t-butyl-5-methylphenol))carbonate, average molecular weight 1300

No. 7

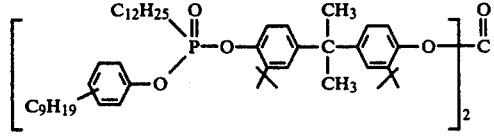

Bis(O-nonylphenyl P-dodecanephosphonate of 4,4′-isopropylidene-bis(2-t-butylphenol)) carbonate, average molecular weight 1800

No. 8

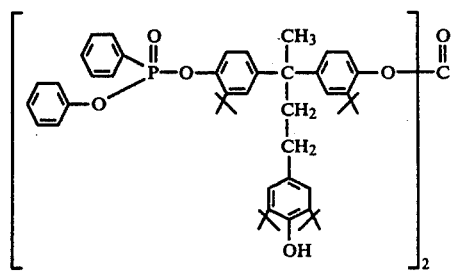

Bis(O-phenyl P-benzenephosphonate of 1(3,5-di-t-butyl-4-

TABLE 1-continued hydroxyphenyl) 3,3-bis(3'-t-butyl-4'-hydroxyphenyl)butane)
carbonate average molecular weight 1600

No. 9

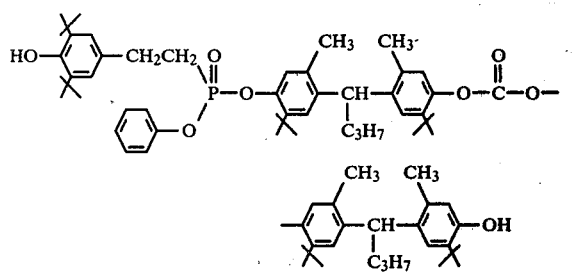

O-Phenyl-P(3,5-di-t-butyl-4-bydroxyphenyl ethane)mono phosphonate of
4,4'-n-dutylidene bis(2-t-butyl-5-methylpehnol)carbonate
average molecular weight 1200

No. 10

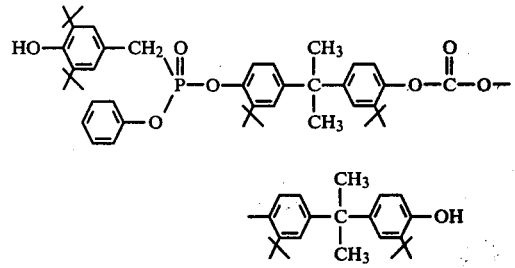

O-Phenyl-P(3,5-di-t-butyl-4-hydroxyphenylmethane)monophosphonate
of 4,4'-isopropylidene bis(2-t-butylphenol)carbonate average
molecular weight 1100

No. 11

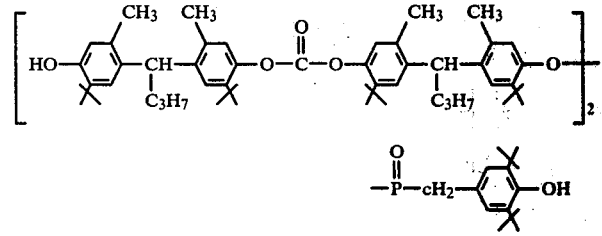

Bis(4,4'-n-butylidene bis(2-t-butyl-5-methylphenol)carbonate)
P-3,5-di-t-butyl-4-hydroxyphenylmethanephosphonate, average
molecular weight 1800

No. 12

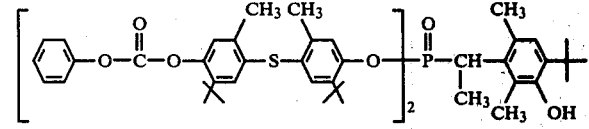

Bis(4'-phenoxycarbonyloxy-2'-methyl-5'-t-butylphenylthio-
2-methyl-5-t-butylphenyl)P-1(2,6-dimethyl-3-hydroxy-4-t-
butylphenyl)ethanephosphonate, average molecular weight 1200

No. 13

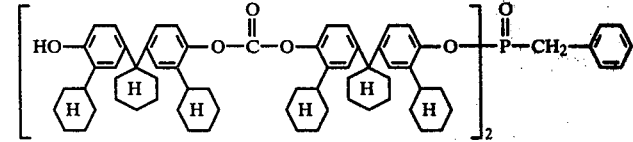

Bis(4,4'-cyclohexylidenebis(2-cyclohexylphenol)carbonate)
P-phenylmethanephosphonate, average molecular weight 1900

No. 14

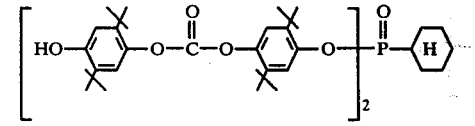

Bis(2,5-di-t-butylhydroquinone carbonate)P-cyclohexane
phosphonate, average molecular weight 1100

TABLE 1-continued

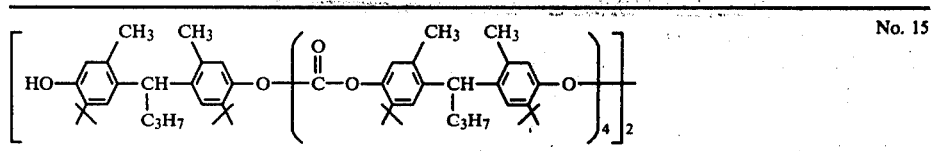

No. 15

Bis(4,4'-n-butylidenebis(2-t-butyl-5-methylphenol)5:4 molar ratio carbonate) P(3,5-di-t-butyl-4-hydroxyphenyl)methanephosphonate, average molecular weight 4300

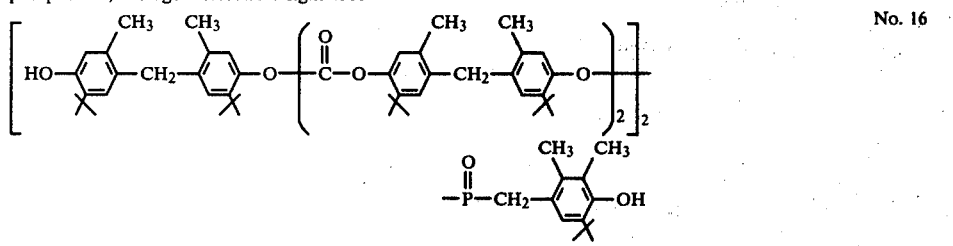

No. 16

Bis(4,4'-methylenebis(2-t-butyl-5-methylphenol)3:2 molar ratio carbonate) P(2,3-dimethyl-4-hydroxy-5-t-butylphenyl) methane phosphonate, average molecular weight 2400

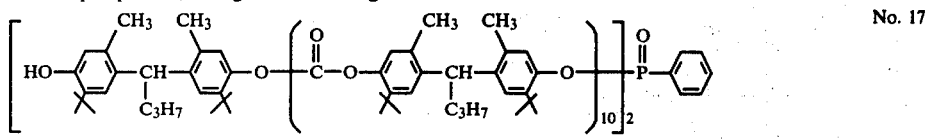

No. 17

Bis(4,4'-n-butylidenebis(2-t-butyl-5-methylphenol)11:10 molar ratio carbonate) P-benzenephosphonate, average molecular weight 9000

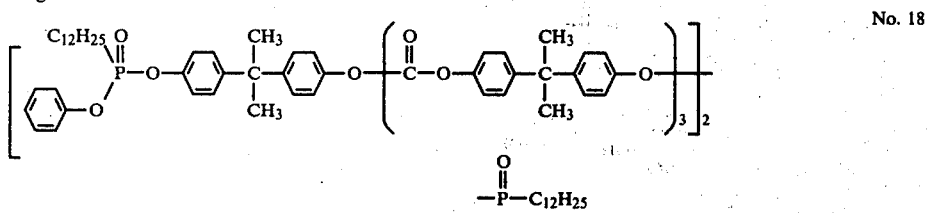

No. 18

Bis(4,4'-isopropylidenephenol mono-O-phenyl-P-dodecanephosphonate) 4:3 molar ratio carbonate) P-dodecanephosphonate, average molecular weight 2700

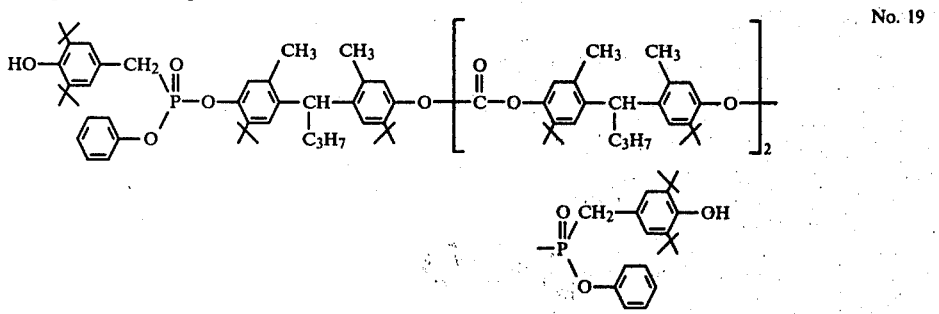

No. 19

4,4'-n-Butylidenebis(2-t-butyl-5-methylphenol) 3:2 molar ratio carbonate bis(O-phenyl-P(3,5-di-t-butyl-4-hydroxyphenyl) methanephosphonate), average molecular weight 1900

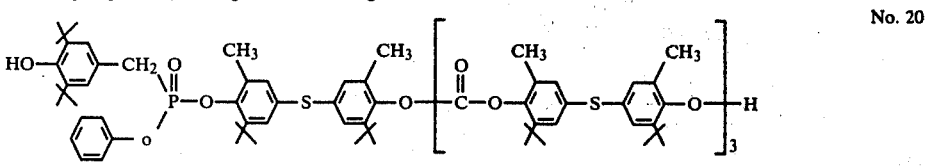

No. 20

4,4'-Thiobis(2-t-butyl-5-methylphenol)4:3 molar ratio carbonate O-phenyl-P(3,5-di-t-butyl-4-hydroxyphenyl) methanephosphonate, average molecular weight 1900

TABLE 1-continued

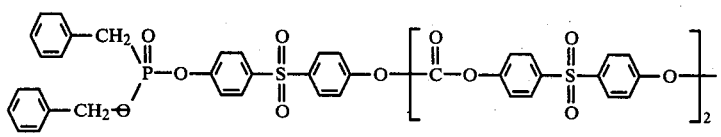
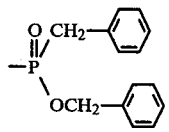

No. 21

4,4'-Sulfonyldiphenol 3:2 molar ratio carbonate bis(O-benzyl-P-phenylmethanephosphonate) average molecular weight 1300

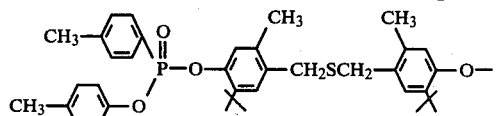

No. 22

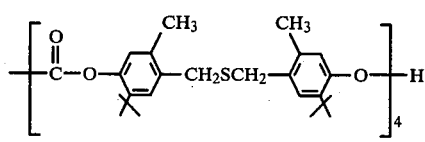

Bis(2-methyl-4-hydroxy-5-t-butylbenzyl)sulfide 5:4 molar ratio carbonate) O-p-tolyl-P-p-toluenephosphonate, average molecular weight 2300

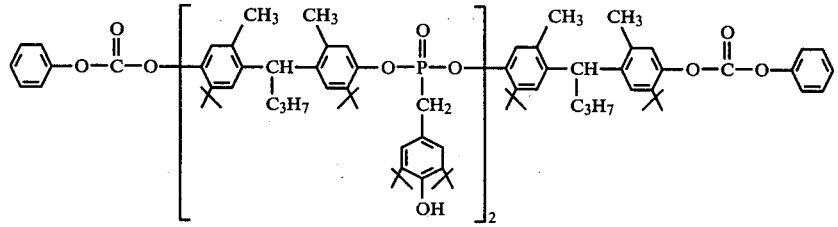

No. 23

4,4'-n-Butylidenebis(2-methyl-5-t-butylphenyl)O,O'-bis(4'-phenoxycarbonyloxy-2'-methyl-5'-t-butyl-alphapropylbenzyl-2-t-butyl-5-methylphenyl)P,P'-bis(3,5-di-t-butyl-4-hydroxyphenyl)methanephosphonate, average molecular weight 1900

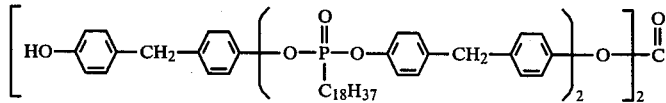

No. 24

Bis(4,4'-methylenebisphenol 3:2 molar ratio P-octadecanephosphonate) carbonate, average molecular weight 2300

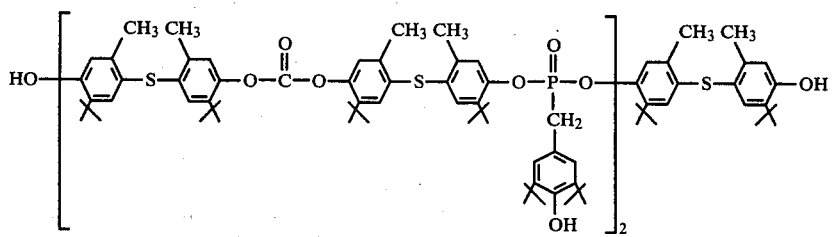

No. 25

4,4'-Thiobis(2-t-butyl-5-methylphenol)carbonate-P(3,5-di-t-butyl-4-hydroxyphenyl)methanephosphonate, 5:2:2 molar ratio, average molecular weight 2400

EXAMPLES 1-1 to 1-7

Substantially unstabilized polypropylene resin (Profax 6501, containing a trace of BHT antioxidant to protect the polymer during shipment and a storage only) 100 parts by weight and Table 1 compound or other stabilizer sample being tested 0.3 part by weight were mixed for ten minutes by mixing and grinding at room temperature and milled and molded to make a sheet of 1.0 mm in thickness at 180° C. and 200 kg./cm² for 5 minutes. From this sheet were cut ten sample pieces of 10×20 mm of each formulation, and exposed on aluminum foil in a Geer air-circulating oven at 160° C. for heat stability examination. The time to the beginning of degradation was taken as the time when more then five sample pieces in ten of each formulation were discolored and brittle.

The stabilizer samples tested and the results obtained are shown in Table-2.

TABLE 2

| NO. CONTROL | STABILIZER | DETERIORATION BEGINNING TIME |
|---|---|---|
| 1-1 | BHT | 20 hours |
| 1-2 | 4,4'-n-butylidenebis (3-methyl-6-t-butyl-phenol) | 85 hours |
| 1-3 | distearyl 3,5-di-t-butyl-4-hydroxybenzyl phosphonate | 185 hours |

| Example | polyhydric phenol organophosphonate-carbonate from Table 1 | |
|---|---|---|
| 1-1 | No. 1 | 480 hours |
| 1-2 | No. 4 | 455 |
| 1-3 | No. 6 | 420 |
| 1-4 | No. 10 | 450 |
| 1-5 | No. 13 | 445 |
| 1-6 | No. 19 | 475 |
| 1-7 | No. 23 | 455 |

Each of the polypropylene samples of Examples 1-1 through 1-7 stabilized according to this invention with a coester of carbonic acid and an organophosphonic acid with a polyhydric phenol had more than double the heat stability of a control composition containing a conventional phenolic phosphonate stabilizer.

EXAMPLES 2-1 to 2-7

Using the same compounding method described above, 1 mm thick test speciments of 10×20 mm were prepared according to the following formulation. Heat stability was measured in a Geer oven at 160° C. and light stability by irradiating with a mercury vapor lamp until signs of failure by embrittlement were noted.

Results are shown in Table 3.

| (FORMULATION) | |
|---|---|
| Polypropylene (Profax 6501) | 100 parts |
| Ca-stearate | 0.2 |
| DLTDP | 0.3 |
| bis(2,2,6,6-tetramethyl-4-piperidinyl)sebacate | 0.3 |
| Stabilizer being tested | 0.1 |

TABLE 3

| NO. Control | STABILIZER | LIGHT STABILITY hrs. | HEAT STABILITY hrs. |
|---|---|---|---|
| 2-1 | None | 175 | 20 |
| 2-2 | Stearyl-beta-(3,5-di-t-butyl-4-hydroxy-phenyl) propionate | 205 | 280 |
| 2-3 | Diethyl(3,5-di-t-butyl-4-hydroxybenzyl)-phosphonate | 250 | 275 |

| Example | Polyhydric phenol organophosphonate-carbonate coester | | |
|---|---|---|---|
| 2-1 | No. 3 | 530 | 805 |
| 2-2 | No. 9 | 485 | 750 |
| 2-3 | No. 11 | 515 | 795 |
| 2-4 | No. 15 | 520 | 780 |
| 2-5 | No. 17 | 470 | 720 |
| 2-6 | No. 20 | 495 | 765 |
| 2-7 | No. 25 | 505 | 760 |

The results show that the conventional phenolic and phenolic phosphonate stabilizers (controls 2-2 and 2-3) contribute only a little to light stability, as shown by the modest increase over Control 2-1. In contrast, the coesters of this invention reinforce the effectiveness of the piperidine stabilizer present to provide approximately twice the time to failure. In the heat stability test, the polymer containing coester stabilizers of this invention lasts more than twice as long as the nearest conventionally stabilized polymer.

EXAMPLES 3-1 to 3-7

Polyethylene resin (Hi-Zex 5100 E, Mitsui Petrochemical Industries, Ltd. Japan) 100 parts by weight, distearylthiodipropionate 0.3 part, BHT 0.1 part, and a polyhydric phenol organophosphonic acid-carbonate coester 0.1 part by weight were milled on a two roll mill for 5 minutes at 150° C. and then molded into a sheet of 1.2 mm thickness by compression molding at 150° C. and 180 kg/cm² for 5 minutes. The sheet was cut into sample pieces of 10×20 mm and tested for heat stability in the Geer oven at 150° C. in air on aluminum foil and for light stability in the Weatherometer. The time to the beginning of degradation was taken as the time when more than five sample pieces in ten of each formulation were discolored or embrittled. The stabilizer ingredients used and the results obtained are shown in Table 4.

TABLE 4

| NO. Control | STABILIZER | LIGHT STABILITY Hours | HEAT STABILITY Hours |
|---|---|---|---|
| 3-1 | None | 135 | 160 |
| 3-2 | 2-hydroxy-4-methoxy benzophenone | 520 | 165 |

| Example | Polyhydric phenol organophosphonate-carbonate coester | | |
|---|---|---|---|
| 3-1 | No. 1 | 945 | 525 |
| 3-2 | No. 5 | 860 | 465 |
| 3-3 | No. 8 | 875 | 480 |
| 3-4 | No. 12 | 905 | 485 |
| 3-5 | No. 16 | 915 | 500 |
| 3-6 | No. 21 | 820 | 440 |
| 3-7 | No. 24 | 825 | 455 |

Each of the polyethylene samples of Examples 3-1 through 3-7 stabilized according to this invention with a coester of carbonic acid and an organophosphonic acid with a polyhydric phenol had a 58 to 82% greater light stability than Control 3-2 stabilized instead with a known benzophenone ultraviolet stabilizer.

EXAMPLES 4-1 to 4-8

ABS resin (Blendex III) 100 parts by weight, Zinc stearate 0.5 part by weight, and a polyhydric phenol organophosphonic acid-carbonate coester 0.3 part by weight were mixed by grinding at room temperature for 10 minutes.

The compound was prepared by extruding the ground mixture using a 30 mm extruder at 30 rpm and 240° C. A sheet of 0.5 mm thickness was prepared by compression molding each extruded compound at 200 kg/cm² and 180° C. for 5 minutes.

The whiteness index of this sheet after heating at 135° C. for 20 hours in a Geer oven, was measured using Hunter color difference meter. The tensile strength retention was measured after irradiating for 800 hours in the Weatherometer.

The results of these tests are shown in Table 5.

TABLE 5

| NO. Control | STABILIZER | WHITE-NESS | TENSILE STRENGTH RETENTION % |
|---|---|---|---|
| 4-1 | None | 0.12 | — |
| 4-2 | 1,1,3-tris(2-methyl-4-hydroxy-5-t-butyl-phenyl)butane | 0.18 | 33 |
| Example. | Polyhydric Phenol Organophosphonate-Carbonate Coester | | |
| 4-1 | No. 2 | 0.31 | 83 |
| 4-2 | No. 3 | 0.38 | 88 |
| 4-3 | No. 7 | 0.29 | 80 |
| 4-4 | No. 11 | 0.37 | 87 |
| 4-5 | No. 14 | 0.32 | 84 |
| 4-6 | No. 18 | 0.28 | 78 |
| 4-7 | No. 22 | 0.32 | 83 |
| 4-8 | No. 25 | 0.35 | 90 |

Each of the ABS polymer samples of Examples 4-1 through 4-8 stabilized according to this invention with a coester of carbonic acid and an organophosphonic acid with a polyhydric phenol had more than double the retained tensile strength of a control sample stabilized with the same zinc stearate as in Examples 4-1 through 4-8 along with a conventional polyhydric phenol stabilizer.

EXAMPLES 5-1 to 5-8

A clear sheet was prepared by kneading polyvinylchloride resin (Geon 103EP) 100 parts, dioctylphthalate 42 parts, epoxidized soybean oil 3 parts, zinc stearate 0.3 parts, barium stearate 0.5 part, stearic acid 0.3 part, and a polyhydric phenol organophosphonic acid-carbonate coester 0.3 part on a two roll mill at 175° C. for 5 minutes and then compression molding at 175° C. Then, a heat stability test was carried out in a Geer oven at 190° C. in an air atmosphere and light stability was measured in the Weather-o-meter. The time to degradation was determined by the discoloration observed. The polyhydric phenol coester used and the results obtained at shown in Table 6.

TABLE 6

| NO. Control | SAMPLE | BEGINNING TIME OF DETERIORATION | | LIGHT STABILITY Hrs. |
|---|---|---|---|---|
| | | YELLOWED Min. | BLACKENED Min. | |
| 5-1 | None | 30 | 45 | 105 |
| 5-2 | Diphenyl isodecyl phosphite | 45 | 60 | 230 |
| Ex. | Polyhydric phenol carbonate-organophosphonate coester | | | |
| 5-1 | No. 1 | 75 | 105 | 510 |
| 5-2 | No. 4 | 60 | 90 | 480 |
| 5-3 | No. 9 | 60 | 90 | 465 |
| 5-4 | No. 12 | 60 | 90 | 490 |
| 5-5 | No. 15 | 75 | 105 | 505 |
| 5-6 | No. 16 | 60 | 75 | 450 |
| 5-7 | No. 19 | 75 | 105 | 510 |
| 5-8 | No. 22 | 60 | 75 | 455 |

Each of the polyvinyl chloride samples of Examples 5-1 through 5-8 stabilized according to this invention with a coester of of carbonic acid and an organophosphonic acid with a polyhydric phenol, along with epoxidized soybean oil, zinc stearate, and barium stearate, had at least 33% greater heat stability than a control sample containing a conventional organic phosphite along with the same epoxidized soybean oil, zinc stearate, and barium stearate, and also approximately double the light stability.

EXAMPLES 6-1 to 6-6

Test pieces were prepared from polybutylene-terephthalate 100 parts and sample (Table 7) 0.2 part by injection molding. The tensile strength retention of the test pieces after irradiating for 500 hours in a Weather-O-Meter was measured, and the tensile strength retention of the test pieces after heating at 150° C. for 240 hours was measured.

The results are shown in Table-7.

TABLE 7

| NO. Control | SAMPLE | TENSILE STRENGTH RETENTION | |
|---|---|---|---|
| | | AFTER IRRADIATING % | AFTER HEATING % |
| 6-1 | None | 53 | 57 |
| Ex. | Polyhydric phenol organophosphonate-carbonate coester | | |
| 6-1 | No. 3 | 82 | 81 |
| 6-2 | No. 10 | 77 | 75 |
| 6-3 | No. 13 | 75 | 76 |
| 6-4 | No. 17 | 78 | 75 |
| 6-5 | No. 20 | 77 | 74 |
| 6-6 | No. 25 | 80 | 79 |

The improvement in retention of tensile strength after both light exposure and heat aging resulting from the use of the coesters of this invention is evident from the above test data.

EXAMPLES 7-1 to 7-7

In order to examine the effects of the compounds according to this invention in ethylene-vinyl acetate copolymer, samples were prepared according to the following formulation and tested for heat stability in a Geer oven at 170° C. and initial color was measured for yellowness using Hunter color difference meter, greater numbers indicating more severe discoloration. Also the tensile strength retention after irradiating 500 hours in a Weather-O-Meter was measured.

The results are shown in Table-8.

(FORMULATION)

| | |
|---|---|
| Ethylene-vinyl acetate copolymer | 100 parts |
| Montan wax lubricant | 0.3 |
| Sample compound (Table 8) | 0.1 |

TABLE 8

| NO Control | SAMPLE | TENSILE STRENGTH RETENTION % | HEAT STABILITY Min. | INITIAL COLOR |
|---|---|---|---|---|
| 7-1 | None | 50 | 60 | 0.32 |
| Ex. | Polyhydric phenol organophosphonate-carbonate coester | | | |
| 7-1 | No. 1 | 82 | 120 | 0.11 |
| 7-2 | No. 3 | 83 | 120 | 0.12 |
| 7-3 | No. 9 | 77 | 105 | 0.14 |
| 7-4 | No. 11 | 80 | 120 | 0.12 |
| 7-5 | No. 15 | 82 | 120 | 0.10 |
| 7-6 | No. 19 | 80 | 105 | 0.13 |
| 7-7 | No. 25 | 81 | 120 | 0.11 |

Each of the ethylene-vinylacetate copolymer samples of Example 7-1 through 7-7 stabilized according to this invention with a coester of carbonic acid and an organophosphonic acid with a polyhydric phenol had much lighter initial color and at least 75% greater heat stability than an unstabilized control sample, as well as 54% at least greater retention of tensile strength.

We claim:

1. As a new composition of matter, a coester having a molecular weight below 10,000, of at least one polyhydric phenol having 2 to 3 phenolic hydroxyl groups and 1 to 3 non-condensed benzenoid rings, with carbonic acid and an organophosphonic acid having the formula

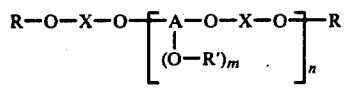

in which
R is an alkyl, cycyloalkyl, aralkyl, aryl, or alkaryl group or the group —A—$(OH)_{m+1}$;
X independently at each occurrance

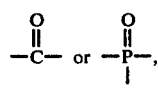

provided that at least one X is

and at least one X is

A is a residue of a dihydric or trihydric phenol;
R' is a hydrogen atom or —X—O—R;
R" is

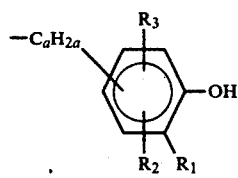

$R_1$ is an alkyl group,
$R_2$ and $R_3$ are hydrogen or alkyl,
a is an integer from 1 to 8,
m is zero or one, and n is an integer from 1 to 20.

2. A coester according to claim 1 in which the molar proportions of carbonic acid to organophosphonic acid range from 20:1 to 1:20.

3. A coester according to claim 1 having a molecular weight between 1000 and about 9000.

4. A coester according to claim 1 in whcih the organophosphonic acid is an alkylhydroxyphenylalkane-phosphonic acid.

5. A coester according to claim 1 in which the polyhydric phenol is 2,5-di-t-butylhydroquinone.

6. A coester according to claim 1 in which the polyhydric phenol has 3 benzenoid rings in the molecule.

7. A coester according to claim 1 in which the polyhydric phenol is an alkylidenebisphenol.

8. A coester according to claim 1 in which the polyhydric phenol is a bis-phenol with two benzenoid rings linked through sulfur.

9. A coester according to claim 1 having the formula

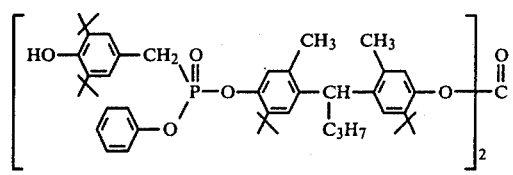

10. A coester according to claim 1 having the formula

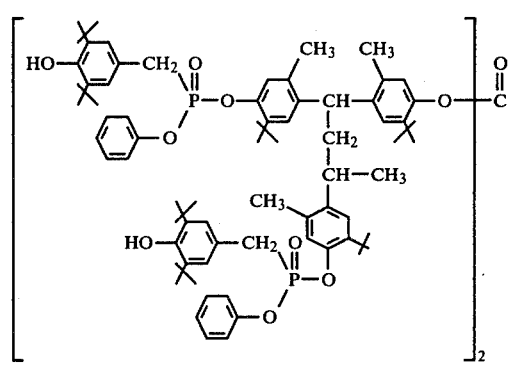

11. A stabilizer composition capable of increasing the resistance to deterioration on heating of a synthetic resin, comprising a coester as defined in claim 1 having a molecular weight below 10,000, of at least one polyhydric phenol having 2 to 3 phenolic hydroxyl groups and 1 to 3 non-condensed benzenoid rings, with carbonic acid and an organophosphonic acid having linked to phosphorus through carbon an organic groups having 1 to about 25 carbon atoms and not more than one phenolic hydroxyl group, in which the molar proportions of carbonic acid to organophosphonic acid range from 20:1 to 1:20, and per part of coester from 1 to about 30 parts of at least one synthetic resin stabilizer selected from the group consisting of thiodipropionate esters, 1,2-epoxides, organic phosphites, polyhydric alcohols, polyhydric alcohol 3-alkylthiopropionates, ultraviolet stabilizers, heavy meatl deactivators, and barium, calcium, magnesium, nickel, strontium, tin, and zinc salts monocarboxylic acids having 6 to 24 carbon atoms.

12. A stabilizer composition according to claim 11 in which the synthetic resin stabilizer is a thiodipropionate ester.

13. A stabilizer composition according to claim 11 in which the synthetic resin stabilizer is a 1,2-epoxide.

14. A stabilizer composition according to claim 11 in which the synthetic resin stabilizer is a 2,2,6,6-tetraalkylpiperidine-4-alcohol carboxylic acid ester having a piperidine nitrogen content for 2 to 8% by weight.

15. A stabilized synthetic resin composition comprising a synthetic resin and 0.001 to 5% by weight of the resin of a coester according to claim 1.

16. A stabilized synthetic resin composition according to claim 1 in which the synthetic resin is selected from the group consisting of olefin polymers, vinyl chloride polymers, acrylonitrile copolymers and polyesters.

* * * * *